United States Patent [19]

Takeshita et al.

[11] Patent Number: 5,166,451

[45] Date of Patent: Nov. 24, 1992

[54] TREATMENT OF HYDROPEROXIDE MIXTURE

[75] Inventors: Akira Takeshita; Shinzaburo Masaki, both of Ooita; Osamu Maruyama, Misawa, all of Japan

[73] Assignee: Sumitomo Chemical Company, Limited, Osaka, Japan

[21] Appl. No.: 737,237

[22] Filed: Jul. 29, 1991

Related U.S. Application Data

[63] Continuation of Ser. No. 280,726, Dec. 6, 1988, abandoned, which is a continuation-in-part of Ser. No. 71,253, Jul. 8, 1987, abandoned.

[30] Foreign Application Priority Data

Jul. 30, 1986 [JP] Japan ................................. 61-17952

[51] Int. Cl.$^5$ .......................................... C07C 409/00
[52] U.S. Cl. .................................................. 568/576
[58] Field of Search ........................................ 568/576

[56] References Cited

U.S. PATENT DOCUMENTS 4,584,413 4/1986 Thornton et al. .................... 568/576
4,891,101 1/1990 Sullivan ............................... 568/576

FOREIGN PATENT DOCUMENTS 0046405 2/1982 European Pat. Off. ............. 568/576
39-22954 10/1964 Japan .................................... 568/576
1232710 5/1977 United Kingdom ................. 568/576

Primary Examiner—Jose G. Dees
Assistant Examiner—B. Frazier
Attorney, Agent, or Firm—Wenderoth, Lind & Ponack

[57] ABSTRACT

Method of treating a hydroperoxide mixture containing both a primary and tertiary aromatic hydroperoxide, by treating the mixture with an alkali and an organic quaternary ammonium salt. This treatment selectively reduces the content of the primary hydroperoxide in the mixture.

9 Claims, No Drawings

TREATMENT OF HYDROPEROXIDE MIXTURE

This application is a continuation of now abandoned application Ser. No. 07/280,726 filed Dec. 6, 1988, which is a continuation-in-part of now abandoned application Ser. No. 07/071,253 filed Jul. 8, 1987.

The present invention relates to a method of treating a hydroperoxide mixture containing an aromatic primary hydroperoxide and an aromatic tertiary hydroperoxide, to selectively reduce the content of the aromatic primary hydroperoxide.

The process for the production of phenols by the acid decomposition of a hydroperoxide obtained by the liquid phase oxidation of an alkyl aromatic compound is industrially useful as a process for the production of phenols, cresols, hydroquinones, resorcinols, etc.

In the liquid phase oxidation of an aromatic compound, where the aromatic compound used is that containing two or more different alkyl groups, it is often the case that a mixture of two or more different hydroperoxides in which the alkyl groups have been hydroperoxidized respectively is obtained, and therefore, if such a mixture is used as such as the starting material for the production of phenols, etc. as described above, there would sometimes be disadvantages, for example, undesired compounds are produced, the reaction is adversely influenced and so forth.

For example, the liquid phase oxidation of cymene produces a mixture of a primary hydroperoxide, i.e., the compound wherein the methyl groups have been oxidized, and a tertiary hydroperoxide, i.e., the compound wherein the isopropyl groups have been oxidized. When this mixture is subjected to the acid decomposition, the teriary hydroperoxide yields cresol and acetone while the primary hydroperoxide yields isopropylphenol and formaldehyde.

However, since the formaldehyde produced from the primary hydroperoxide reacts with the cresol under the acid decomposition conditions to form a resinous substance, the cresol yield from the tertiary hydroperoxide is markedly reduced. Therefore, it is desired to separate and remove the primary hydroperoxide prior to the acid decomposition or to convert the primary hydroperoxide into a substance which does not react with cresol, but under the present situation, no process has been discovered which is advantageous from an industrial point of view.

For example, a method of selectively decomposing a primary hydroperoxide by directly treating the above-mentioned hydroperoxide mixture with a basic compound has been proposed in, e.g. U.S. Pat. No. 2,728,797, Japanese Patent Publication No. 12183/77, etc. However, if an alkali metal compound is used as the basic compound, when the primary hydroperoxide compound is decomposed to a great extent, there are such problems that it is impossible to satisfactorily inhibit the decomposition of the tertiary hydroperoxide, and the decomposition speed is slow. Further, this method comprising adding an alkali as its solution in, e.g. alcohol, renders the operations complicated, because it is necessary to remove the alcohol in addition to the removal of the alkali in the post-treatment step.

On the other hand, Japanese Patent Publication No. 12183/77 discloses a method comprising contacting a hydroperoxide mixture and an alkali aqueous solution at high temperature, but in spite of its advantage of being capable for high-speed treatment, there has been much to be improved in the enhancement of the percent of the aromatic primary hydroperoxide decomposed.

The present inventors have been intensively studying in order to improve the disadvantages concerning the operations and the yields in these prior art techniques, and have finally come to discover the method of the present invention.

Accordingly, the present invention is a method of treating a hydroperoxide mixture which is characterized by treating a hydroperoxide mixture containing an aromatic primary hydroperoxide and an aromatic tertiary hydroperoxide in the presence of an alkali and an organic quaternary ammonium salt.

The purpose of the present invention resides in the selective reduction of the content of the aromatic primary hydroperoxide in the above-described hydroperoxide mixture, and this may be accomplished by treating the mixture in the presence of an alkali and an organic quaternary ammonium salt according to the present invention.

The present invention is now described in detail.

HYDROPEROXIDE MIXTURE

The aromatic primary hydroperoxide in the present invention is a compound of the general formula:

$$ArCH_2OOH$$

wherein Ar represents a substituted or unsubstituted aromatic group, and specific examples thereof are as follows:

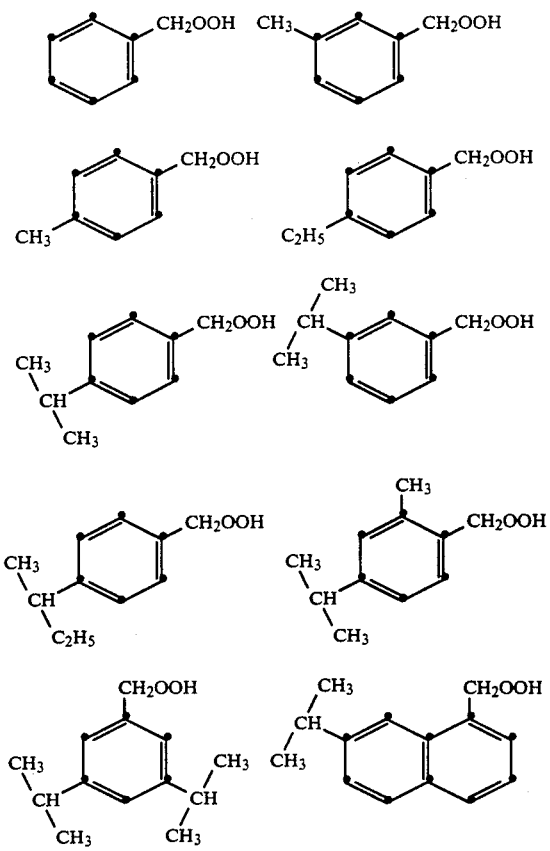

-continued

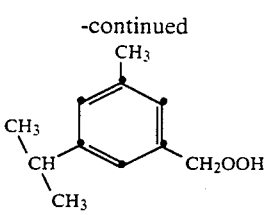

On the other hand, the aromatic tertiary hydroperoxide is a compound of the general formula:

wherein Ar' represents a substituted or unsubstituted aromatic group, and specific examples thereof are as follows:

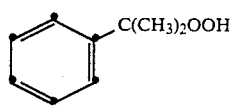

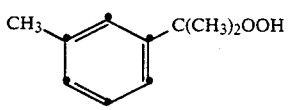

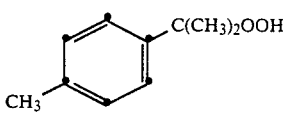

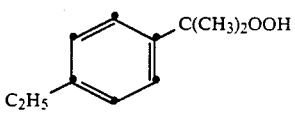

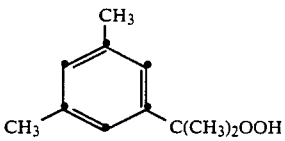

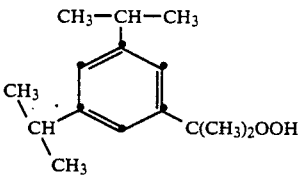

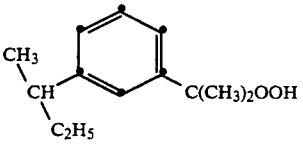

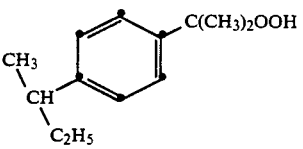

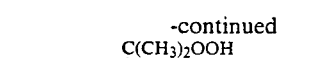

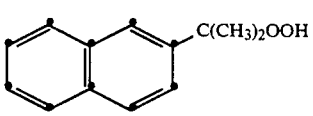

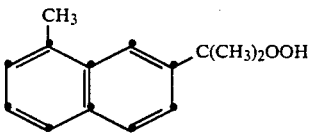

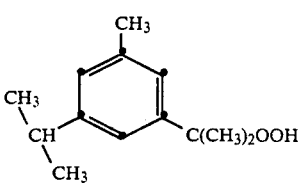

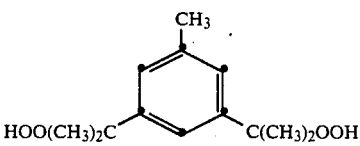

While the mixing ratio of the aromatic primary hydroperoxide to the aromatic tertiary hydroperoxide is not restricted, it is generally preferred to use a mixture of 3-30 parts by weight, in particular 5-25 parts by weight, of the aromatic primary hydroperoxide and correspondingly, 97-70 parts by weight, in particular 95-75 parts by weight, of the aromatic tertiary hydroperoxide (the sum of both being 100 parts by weight). Typical examples of the above-described mixture are those obtained by oxidizing an aromatic compound containing a methyl group and an isopropyl group in the aromatic moiety with oxygen or an oxygen-containing gas in the liquid phase and separating the oxidation product by such proper operation as phase separation and recovery as an oily layer, as well as concentrates thereof. For example, there may be illustrated those obtained by the oxidation of m-cymene, p-cymene, m, p-mixed cymenes, 2,4-dimethylisopropylbenzene, 3,5-dimethylisopropylbenzene, 1-methyl-7-isopropylnaphthalene, etc. and subsequent separation and recovery as oily layers and their concentrates.

The mixture of the aromatic primary hydroperoxide and the aromatic tertiary hydroperoxide may be diluted with hydrocarbons such as benzene, toluene, ethylbenzene, cumene, xylene, cymene, diisopropylbenzene, etc., and ketones such as acetone, methyl ethyl ketone, methyl isobutyl ketone, etc. In such a case, it is desired that the hydroperoxide concentration be adjusted to 1-95% by weight, particularly preferably 5-90% by weight.

The above-described oxidation products of the aromatic hydrocarbons containing the methyl group and the isopropyl group or concentrates thereof are generally in the form diluted with the starting material aromatic hydrocarbon. Said oxidized product may be either that which has been oxidized in the absence of water or that which has been oxidized in the presence of an alkali aqueous solution.

However, after the oxidation reaction and before the treatment with alkali and organic quaternary ammonium salt in accordance with the present invention, it is necessary to remove the various by-products formed in the course of the oxidation reaction. Thus, when the oxidation reaction has been conducted in non-aqueous system the resulting reaction mixture is washed, for example, with water. When the oxidation reaction has been conducted in the presence of an alkali aqueous solution the resulting reaction mixture is separated into an oily layer and aqueous layer and the oily layer is recovered. Thus the hydroperoxide mixture to be treated in accordance with the present invention, as oxidation reaction product, consists essentially of a primary hydroperoxide and tertiary hydroperoxide and hence substantially free from side-products formed in the course of the oxidation reaction.

ALKALI

The alkali used in the present invention is generally added in the form of an aqueous solution. However, if the oxidation product is that obtained in the presence of an aqueous solution, the predetermined amount of the alkali is added in the form of either powder or highly concentrated solution.

Examples of the alkali which may be used include alkali metal hydroxides and alkaline earth metal hydroxides such as sodium hydroxide, potassium hydroxide, lithium hydroxide, calcium hydroxide, barium hydroxide, magnesium hydroxide, strontium hydroxide, etc. Of those, the hydroxides easily soluble in water such as sodium hydroxide, potassium hydroxide, lithium hydroxide, etc. are especially preferred. They may be used either singly or as a mixture of two or more thereof.

Further, in addition to the above-mentioned alkalis, it is also possible to use buffers of these with sodium carbonate, sodium bicarbonate, etc.

If the above-mentioned hydrocarbons are used as preferred diluents for said hydroperoxide mixture, these alkali aqueous solutions may be allowed to stand after the contacting treatment, thereby each treating solution may be easily separated. After separation, it may also be re-used by adjusting the concentration. Further, since the amount of the alkali remaining in the organic layer is small by this separation, only an extremely small quantity of water or an acid aqueous solution is required for washing the organic layer.

The ratio of the oil layer containing said hydroperoxide mixture to the alkali aqueous solution differs depending on the mixing conditions according to the type of the apparatus, the mode of agitation, etc., but in general, a range of 0.05-5 of the aqueous layer based on 1 of the oil layer (ratio by weight) is used.

The amount of the alkali used in the present invention is in general 0.1-10 molar ratio, preferably 0.3-5 molar ratio, based on the aromatic primary hydroperoxide.

Where said alkali is added as a solution, it is prepared as an aqueous solution of 0.05-50% by weight.

ORGANIC QUATERNARY AMMONIUM SALT

As the organic quaternary ammonium salt used in the present invention, there may be mentioned quaternary ammonium salts of the general formula (I) or (II):

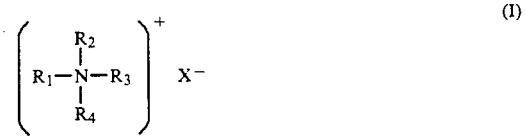

wherein $R_1$ and $R_2$ each represents an alkyl group of 1-24 carbon atoms or an optionally substituted benzyl group, $R_3$ and $R_4$ each represents an alkyl group of 1-10 carbon atoms, and X represents an anion residue;

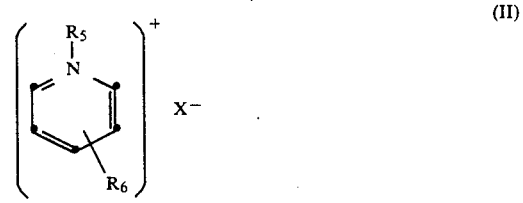

wherein $R_5$ represents an alkyl group of 1-24 carbon atoms, $R_6$ represents a hydrogen atom or a methyl group, and X is as defined above. As the anion residue in the general formulae, there may be mentioned, in addition to chlorine, bromine and iodine, residues of sulfates, phosphates, acetates, methylsulfates, ethylsulfates, perchlorates and bisulfates.

Specific examples of the quaternary ammonium salts include the following compounds:

tetra-n-butylammonium chloride, tetra-n-propylammonium chloride, tetraethylammonium chloride, tetramethylammonium chloride, stearyltrimethylammonium chloride, trimethyloctadecylammonium chloride, lauryltrimethylammonium chloride, trimethylhexadecylammonium chloride, distearyldimethylammonium chloride, dicetyldimethylammonium chloride, tricaprylmethylammonium chloride, o-, m- or p-methoxybenzyltriethylammonium chloride, o-, m- or p-phenoxybenzyltriethylammonium chloride, trimethyldodecylammonium chloride, trimethyldecylammonium chloride, trioctylmethylammonium chloride, stearylamidomethylpyridinium chloride, N-butylpyridinium chloride, laurylpyridinium chloride, laurylpicolinium chloride, triethylpropylammonium chloride, diethlpropylbenzylammonium chloride, trimethylbenzylammonium chloride, triethylbenzylammonium chloride, o-, m- or p-chlorobenzyltriethylammonium chloride, methylethylpropylbenzlammonium chloride, diethylbutylbenzylammonium chloride, methyldiethylbenzylammonium chloride, dimethylethylbenzylammonium chloride, tripropylbenzylammonium chloride, ethyldipropylbenzylammonium chloride, diethyldibenzylammonium chloride, dimethyllaurylbenzylammonium chloride, stearylbenzyldimethylammonium chloride, octylbenzyldimethylammonium chloride, myristylbenzyldimethylammonium chloride, as well as bromides, iodides, sulfates, perchlorates, phosphates, bisulfates, acetates, methylsulfates and ethylsulfates corresponding to these chlorides.

Of course, these organic quaternary ammonium salts can be used singly or in mixtures thereof may also suffice.

The amount of the organic quaternary ammonium salt used is in general 0.01-20% by weight, preferably 0.1-10% by weight, more preferably 0.2-5% by weight, based on the oil layer containing said hydroperoxide mixture.

TREATING CONDITIONS

For the treatment according to the method of the present invention, it is desired that only the aromatic primary hydroperoxide undergo the decomposition reaction, with the change of the aromatic tertiary hydroperoxide being inhibited so as to occur to the minimum extent. For this purpose, it is desired to determine the amounts of the above-described alkali and organic quaternary ammonium salt used, the treating time and the treating temperature so that the percent of the aromatic primary hydroperoxide reacted will be 80% or higher, preferably 90% or higher, and that the percent of the aromatic tertiary hydroperoxide recovered will be 90% or higher, especially 95% or higher.

Although the treating time depends on other conditions, in general, contacting is carried out for 0.1 minute to 10 hours, preferably 0.1 minute to 5 hours. Further, the treating temperature is generally 30° C.–150° C., preferably 50° C.–120° C., more preferably 70° C.–110° C.

In order to enhance the contacting treatment efficiency, it is preferably carried out with stirring. The time to terminate the reaction may be determined by analyzing the contents of the aromatic primary hydroperoxide and the aromatic tertiary hydroperoxide in the reaction mixture by liquid chromatography.

The order of the addition of the alkali and the organic quaternary ammonium salt to the hydroperoxide mixture is not restricted. Further, the treating method may be, in addition to a batchwise reaction mode, a flow type total mixing reaction mode, or a cylinder type reaction mode.

The reaction treatment mode of the present invention is not limited to those described in the examples.

POST-TREATMENT

After the treatment, the stirring is stopped, the alkaline aqueous solution settling down beneath the treating solution is separated, and then the organic layer may be washed with water or an acid aqueous solution.

The reaction mixture thus treated is that in which the aromatic primary hydroperoxide/aromatic tertiary hydroperoxide ratio has been remarkably decreased as compared with the starting material, and therefore when phenols are produced by its acid decomposition, the formation of by-products is small, and thus the yield is high. Further, if used as the starting material for the production of a peroxide, a product having a high purity may easily be obtained with only small amounts of by-products.

As in the present invention, by treating a mixture of hydroperoxides in the presence of an alkali and an organic quaternary ammonium salt, there is a remarkable advantage that the aromatic primary hydroperoxide may be preferentially and selectively decomposed in a short time.

The present invention will be described in more detail by the following examples, but it should be noted that the present invention is not restricted to the following examples unless it departs from its subject matter.

In the examples, the parts and % mean parts by weight and % by weight respectively.

REFERENCE EXAMPLE 1

A two-layer liquid mixture consisting of 690 parts of a cymene mixture (m-cymene 64.7%, p-cymene 32.4% and O-cymene 2.9%) and 50 parts of a 0.5% aqueous alkali solution was subjected to the oxidation reaction at 120° C. for 6 hours while introducing air thereto under stirring. During the oxidation reaction an aqueous alkali solution was continuously introduced into the reaction system to keep the pH of the reaction system constant by neutralization. After the reaction the mixture was left standing for phase separation and the oily layer was recovered. The oxidation product thus obtained contained tertiary cymene hydroperoxide, primary cymene hydroperoxide and unreacted cymene. The total of the primary hydroperoxide and tertiary hydroperoxide (total peroxide concentration) was 12.9%.

EXAMPLE 1

To a four-necked flask fitted with a stirring rod and also equipped with a thermometer and a reflux condenser, 200 parts of cymene oxidation product (total hydroperoxide concentration in the unreacted cymene as a solvent: 12.9%, primary hydroperoxide/total hydroperoxides=10.6%) obtained in Reference Example 1, 2.0 parts of trioctylmethylammonium chloride and 100 parts of a 0.5% sodium hydroxide aqueous solution were added, and stirring was conducted at 80° C. Thirty minutes later, the primary hydroperoxide, the tertiary hydroperoxide and major components were analyzed by liquid chromatography, to find that the primary hydroperoxide had been decomposed 100% (primary, percent decomposed) and the percent of the tertiary hydroperoxide recovered (tertiary, percent recovered) had reached 98.0%.

EXAMPLES 2-5 AND COMPARATIVE EXAMPLES 1-2

Operations similar to those in Example 1 were conducted except that the temperature, the amount of the trioctylmethylammonium chloride added, the amount of the sodium hydroxide added and the oil layer/aqueous layer ratio were changed to the values set forth in Table 1. The results are shown in Table 1 (this also applies hereinafter). Where either of trioctylmethylammonium chloride or alkali is not employed, as shown in Comparative Examples 1 and 2, it takes a longer time to decompose the primary hydroperoxide or the percent of the tertiary hydroperoxide recovered is low.

EXAMPLES 6-7 AND COMPARATIVE EXAMPLE 3

Operations similar to those in Example 1 were conducted except that lithium hydroxide was used instead of the sodium hydroxide, the amount of the lithium hydroxide added being as indicated in Table 1. Also in this case, as shown in Comparative Example 3, where the trioctylmethylammonium chloride is not used, the percent of the tertiary hydroperoxide recovered is low and also it takes a longer time to decompose the primary hydroperoxide.

EXAMPLES 8-9

Operations similar to those in Example 1 were conducted except that potassium hydroxide was used instead of the sodium hydroxide, the amount of the potassium hydroxide added being as indicated in Table 1.

EXAMPLES 10-13

Instead of the trioctylmethylammonium chloride in Example 1, the organic quaternary ammonium salts described in Table 2 were used respectively. Results comparable to those in Example 1 were obtained.

EXAMPLE 14

120 parts of the 10% sodium carbonate aqueous solution and 80 parts of a cymene oxidation product (total hydroperoxide concentration in the unreacted cymene as a solvent: 11.5%, primary hydroperoxide/total hydroperoxides=12.5%) as a reaction initiator were charged to 840 parts of a m-, p-cymene mixture, which was oxidized in air at 115° C. for 8 hours. After the reaction the resulting mixture was left standing for phase separation and the formed oily layer was recovered, to obtain an oxidation product having a total hydroperoxide concentration of 12.0%.

After cooling to 80° C., 6 parts of 28% sodium hydroxide and 4.5 parts of trioctylmethylammonium chloride were added and stirring was conducted at the same temperature for 30 minutes. After allowed to stand, the aqueous layer in the lower layer was removed, and thereafter the oil layer was analyzed by liquid chromatography. As a result, the primary hydroperoxide was hardly detected, and the tertiary hydroperoxide was obtained at a recovery of 97% based on the amount remaining in the oxidation product.

EXAMPLE 15

200 parts of an oxidation product of 1-methyl-7-isopropylnaphthalene (total hydroperoxide concentration: 10.0%, primary hydroperoxide/tertiary hydroperoxide=15.0%) obtained by the oxidation and subsequent separation as oily layer, 2 parts of tetrabutylammonium chloride and 100 parts of a 0.5% sodium hydroxide aqueous solution were added, and stirring was conducted at 80° C. Thirty minutes later, the primary hydroperoxide, the tertiary hydroperoxide and major components were analyzed by liquid chromatography, to find that the primary hydroperoxide had been decomposed 100%, and the percent of the tertiary hydroperoxide recovered had reached 96%.

EXAMPLE 16

200 parts of an oxidation product of 3,5-diisopropyltoluene (total hydroperoxide concentration: 9.5%, primary hydroperoxide/tertiary hydroperoxide=12.0%) obtained by the oxidation and subsequent separation as oily layer, 2 parts of trimethylhexadecylammonium chloride and 100 parts of a 0.5% sodium hydroxide aqueous solution were added, and stirring was conducted at 90° C. Thirty minutes later, the primary hydroperoxide, the tertiary hydroperoxide and major components were analyzed by liquid chromatography, to find that the primary hydroperoxide had been decomposed 98% and the percent of the tertiary hydroperoxide recovered had reached 95%.

TABLE 1

| | Temp. °C. | Organic Quarter. Kind | Ammonium Salt Amount added*1 | Alkali Kind | Alkali Molar Ratio*2 | Oil Layer/ Aq. Layer | Reaction Time (min) | Primary Percent Decomposed | Tertiary Percent Recovered |
|---|---|---|---|---|---|---|---|---|---|
| Ex. 1 | 80 | Trioctylmethylammonium chloride | 1% | NaOH | 0.76 | 2 | 30 | 100% | 98% |
| Ex. 2 | 95 | Trioctylmethylammonium chloride | 0.5 | " | 0.5 | " | " | 100 | 97 |
| Ex. 3 | 60 | Trioctylmethylammonium chloride | " | " | 0.8 | 1 | " | 100 | 97 |
| Ex. 4 | 80 | Trioctylmethylammonium chloride | 1 | " | 0.76 | 10 | " | 100 | 98 |
| Ex. 5 | " | Trioctylmethylammonium chloride | 0.2 | " | 0.6 | " | 120 | 100 | 97 |
| Comp. Ex. 1 | " | Trioctylmethylammonium chloride | 1 | — | — | " | 240 | 10 | 96 |
| Comp. Ex. 2 | 95 | — | — | NaOH | 0.76 | 2 | 180 | 60 | 93 |
| Ex. 6 | 80 | Trioctylmethylammonium chloride | 1 | LiOH | 0.7 | " | 30 | 100 | 97 |
| Ex. 7 | 95 | Trioctylmethylammonium chloride | 0.5 | " | 0.4 | 10 | " | 100 | 96 |
| Comp. Ex. 3 | " | — | — | " | 0.7 | 2 | 240 | 80 | 92 |
| Ex. 8 | " | Trioctylmethylammonium chloride | 1 | KOH | 0.8 | 10 | 60 | 100 | 97 |
| Ex. 9 | 80 | Trioctylmethylammonium chloride | " | " | 1.0 | 0.5 | 30 | 98 | 96 |
| Ex. 10 | 85 | Tetrabutylammonium bromide | 1% | NaOH | 0.76 | 2 | 120 | 97% | 96% |
| Ex. 11 | " | Tetrabutylammonium chloride | " | " | " | " | 10 | 100 | 97 |
| Ex. 12 | " | Tetra-n-propylammonium bromide | " | " | " | " | 180 | 100 | 98 |
| Ex. 13 | " | Trimethylhexadecylammonium chloride | " | " | " | " | 10 | 100 | 97 |

Notes
*1% by weight based on the oil layer
*2Molar ratio to the primary hydroperoxide

TABLE 2

| | Temp. °C. | Organic Quater. Ammonium Salt | | Alkali | | Oil Layer/ Aq. Layer | Reaction Time (min) | Primary Percent Decomposed | Tertiary Percent Recovered |
| --- | --- | --- | --- | --- | --- | --- | --- | --- | --- |
| | | Kind | Amount added[*1] | Kind | Molar Ratio[*2] | | | | |
| Ex. 10 | 85 | Tetrabutylammonium bromide | 1% | NaOH | 0.76 | 2 | 120 | 97% | 96% |
| Ex. 11 | " | Tetrabutylammonium chloride | " | " | " | " | 10 | 100 | 97 |
| Ex. 12 | " | Tetra-n-propylammonium bromide | " | " | " | " | 180 | 100 | 98 |
| Ex. 13 | " | Trimethylhexadecyl-ammonium chloride | " | " | " | " | 10 | 100 | 97 |

Notes
[*1] % by weight based on the oil layer
[*2] Molar ratio to the primary hydroperoxide

What we claim is:

1. A method of treating a hydroperoxide mixture which comprises treating a hydroperoxide mixture consisting essentially of an aromatic primary hydroperoxide and an aromatic tertiary hydroperoxide with an alkali and an organic quaternary ammonium salt, to selectively reduce the content of the aromatic primary hydroperoxide in the mixture.

2. The method according to claim 1 wherein the hydroperoxide mixture is obtained by oxidizing an aromatic compound having a methyl group and an isopropyl group in the aromatic moiety with oxygen or oxygen-containing gas in a liquid phase, allowing the resulting reaction mixture to stand for phase separation and recovering an oily layer, or its concentrate.

3. The method according to claim 1 wherein the hydroperoxide mixture contains 3–30 parts by weight of the aromatic primary hydroperoxide and 97–70 parts by weight of the aromatic tertiary hydroperoxide, the sum of the primary and tertiary hydroperoxides being 100 parts by weight.

4. The method according to any one of claims 1–3 wherein the treatment is carried out in the presence of an alkyl aromatic hydrocarbon.

5. The method according to claim 2 wherein the aromatic compound having a methyl group and an isopropyl group is m-cymene, p-cymene or mixed cymene.

6. The method according to claim 1 wherein the method is conducted in a single reaction vessel.

7. The method according to claim 1 wherein the hydroperoxide mixture is diluted with a hydrocarbon, and the organic quaternary ammonium salt is used in an amount of 0.01–20% by weight based on the combined weight of the hydrocarbon and the hydroperoxide mixture.

8. The method according to claim 7 wherein the amount of the salt is 0.1–20% by weight.

9. The method according to claim 7 wherein the amount of the salt is 0.2–20% by weight.

* * * * *